United States Patent [19]

Kato et al.

[11] Patent Number: 4,929,331
[45] Date of Patent: May 29, 1990

[54] OXYGEN SENSOR

[75] Inventors: Nobuhide Kato, Ama; Yasuhiko Hamada, Nagoya, both of Japan

[73] Assignee: NGK Insulators, Ltd., Japan

[21] Appl. No.: 300,972

[22] Filed: Jan. 24, 1989

[30] Foreign Application Priority Data

Jan. 29, 1988 [JP] Japan ................ 63-9730[U]

[51] Int. Cl.$^5$ .............................................. G01N 27/46
[52] U.S. Cl. .................................... 204/426; 204/428
[58] Field of Search ..................... 204/15, 421–429

[56] References Cited

U.S. PATENT DOCUMENTS

| | | | |
|---|---|---|---|
| 4,323,440 | 4/1982 | Akatsuka | 204/428 |
| 4,559,126 | 12/1985 | Mase et al. | 204/425 |
| 4,597,850 | 7/1986 | Takahasi et al. | 204/426 |
| 4,683,049 | 7/1987 | Nakajima et al. | 204/428 |
| 4,689,136 | 8/1987 | Nakajima et al. | 204/426 |

Primary Examiner—T. Tung
Attorney, Agent, or Firm—Arnold, White & Durkee

[57] ABSTRACT

In an oxygen sensor having a plate-shaped oxygen sensor element, a measuring electrode on the broader width surface of the plate-shaped sensor element, and a protective cover covering the plate-shaped sensor element and having gas inlet holes for introducing a gas to be measured therein, a cylindrical body is provided between the plate-shaped sensor element and the protective cover in such fashion as to avoid direct impingement of the gas to be measured upon the measuring electrode, whereby the oxygen sensor can provide good measurements of the gas with high precision and a constant λ controlling point.

6 Claims, 4 Drawing Sheets

FIG_1
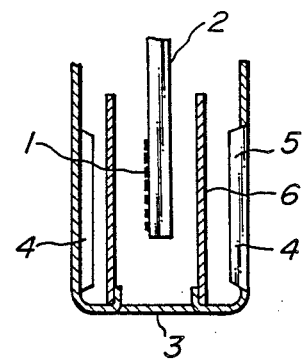
FIG_2a
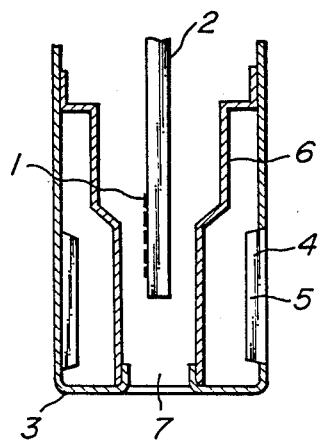
FIG_2b
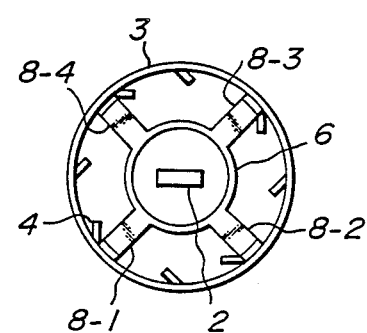

FIG_3a
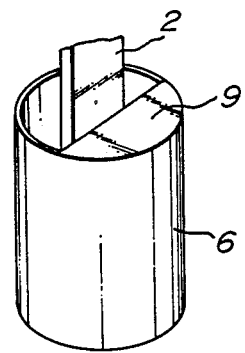
FIG_3b
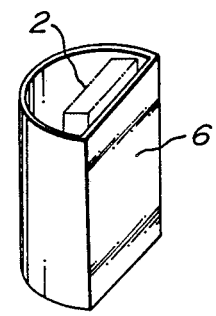
FIG_4a
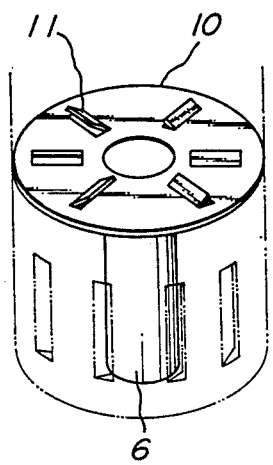
FIG_4b
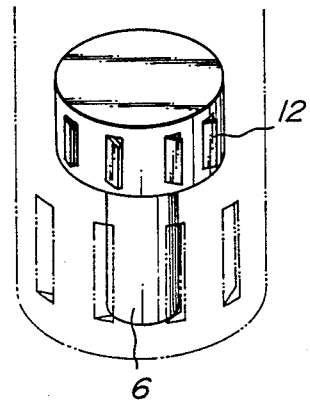

FIG_5a
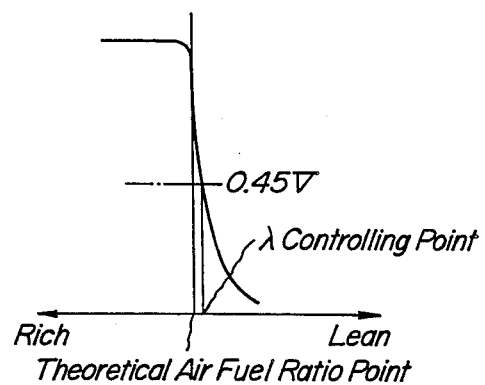
FIG_5b
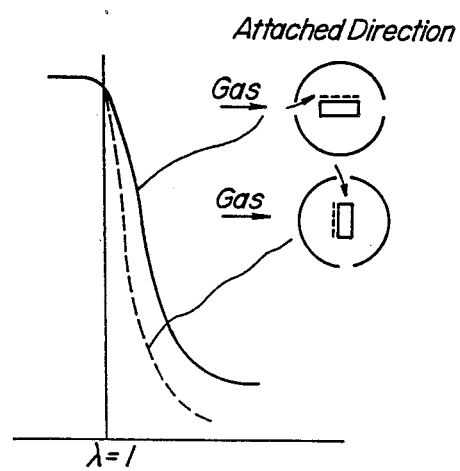

FIG_6a
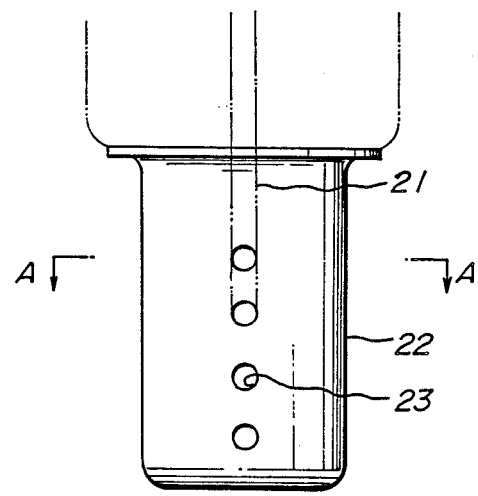
FIG_6b
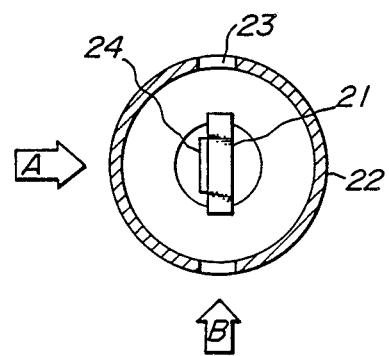

OXYGEN SENSOR

BACKGROUND OF THE INVENTION

1. Field of the Invention

The present invention relates to an oxygen sensor, particularly to an oxygen sensor having a plate-shaped oxygen sensor element.

2. Related Art Statement

Heretofore, in order to improve precision of measurement of an oxygen sensor using a plate-shaped oxygen sensor element, the applicant disclosed in Japanese Utility Model Application Laid-Open No. 60-150,447 an oxygen sensor wherein gas vent holes 23 for ventilating a gas to be measured are positioned on a protective cover 22 protecting a plate-shaped sensor element 21 such that they do not face the surface of the plate-shaped sensor element 21, as shown in the attached FIG. 6(b).

However, in the oxygen sensor of the above Japanese Utility Model Application Laid-Open No. 60-150,447, the measuring electrode 24 is arranged on a broader width surface of the plate-shaped sensor element 21, as shown in the attached FIG. 6(b), so that the oxygen sensor has a drawback in that the gas to be measured impinges differently on the measuring electrode 24 depending on the attached direction of the oxygen sensor. Namely, the gas to be measured impinges in different manners on the measuring electrode 24 of the sensor element 21, depending on the direction A or B of the entrance of the gas in the protective cover 22.

If the manner of impingement of the gas to be measured on the measuring electrode 24 varies just as described above, a measurement of a high precision can not be performed, because the $\lambda$ controlling point of the oxygen sensor varies and the response at the low flow rate of the gas varies by the reasons described later.

SUMMARY OF THE INVENTION

An object of the present invention is to obviate the above drawbacks and problems.

Another object of the present invention is to provide an oxygen sensor having a plate-shaped oxygen sensor element always capable of performing an optimum measurement with a high precision and a constant $\lambda$ controlling point, regardless to an attached direction of the oxygen sensor.

The present invention is an oxygen sensor having a plate-shaped oxygen sensor element, a measuring electrode arranged on the broader width surface of the sensor element, and a protective cover covering the plate-shaped sensor element, the protective cover having gas inlet holes for introducing a gas to be measured therein, comprising, between the protective cover and the plate-shaped oxygen sensor, a cylindrical body having at least one open end and not having a gas-vent hole on the side wall thereof, in such a fashion as to protectively cover the plate-shaped sensor element.

In another aspect of the present invention, the cylindrical body has at least one gas vent hole on the side wall thereof at a position or positions not facing the measuring electrode.

If an outlet hole is provided on the bottom end surface of the protective cover for outletting the gas, and the open lower end of the cylindrical body is communicated with the outlet hole, the flow of the gas after being measured by the measuring electrode is facilitated, so that the present invention can be more suitably effected.

In the present invention, the desired cylindrical body is arranged between the protective cover and the plate-shaped sensor element, so that the gas to be measured supplied through the gas vent holes of the protective cover does not impinge directly on the measuring electrode. Namely, the gas to be measured is introduced at first in the interior of the protective cover along the cylindrical body, and then in the interior of the cylindrical body to contact the measuring electrode, so that the gas to be measured impinges on the measuring electrode always at a constant state, despite the attached direction of the oxygen sensor.

Hereinafter, the reasons will be explained why the $\lambda$ controlling point differs depending on the manners of impingement of the gas to be measured on the measuring electrode. Generally, the $\lambda$ controlling point of an oxygen sensor is shifted slightly to the lean side from the theoretical air-fuel ratio point, as shown in the attached FIG. 5(a). The shift is caused by the following phenomena. Namely, uncombusted components such as CO, hydrocarbons and the like exist in the gas to be measured such as an exhaust gas from automobile engines even if the combustion is effected in a lean (oxygen excess) atmosphere. In an ideal state, the uncombusted components react with the excess oxygen to become an equilibrating gas. In this case, the $\lambda$ controlling point coincides with the theoretical air fuel ratio point. The equilibrating reaction proceeds during the passage of the gas through the coating layer and the platinum layer of the sensor element, and reaches the above ideal state, if it proceeds completely before reaching a three phase interface. However, in practice, the reaction does not proceed completely, and some amounts of the uncombusted components reach the three phase interface and react with $O^{--}$ in $ZrO_2$ of the sensor element to leave, for example, electrons by a reaction of $CO+O^{--}\rightarrow CO_2+2e^-$. That is, an electromotive force is generated at portions of many three phase interfaces where the uncombusted components reach, and hence an electromotive force is flows even in a lean atmosphere, and the $\lambda$ controlling point is apparently shifted to the lean side. Therefore, if the gas to be measured impinges strongly on the measuring electrode, the amount of uncombusted components reaching the three phase interfaces is large, so that the electromotive force becomes high (the shift to the lean side is large). Conversely, if the gas to be measured impinges weakly on the measuring electrode, the vice-versa phenomena occurs. Because the equilibrating reaction of the uncombusted components is promoted with the increase of the temperature, the shift to the lean side becomes small with the increase of the temperature of the gas to be measured (i.e., the temperature of the sensor element). Therefore, the temperature change of the sensor element depending on the manner of impingement of the gas to be measured on the measuring electrode, is also a cause of the change of the $\lambda$ controlling point. As a result, in conventional oxygen sensors the $\lambda$ controlling point varies, depending on the attached direction of the oxygen sensor relative to the flow direction of the gas to be measured, as shown in the attached FIG. 5(b).

BRIEF DESCRIPTION OF THE DRAWINGS

FIG. 1 is a schematic cross sectional view of an example of the oxygen sensor of the present invention;

FIGS. 2(a) and (b) are respectively, a schematic cross sectional view and a schematic plan view of another embodiment of the oxygen sensor of the present invention;

FIGS. 3(a) and (b) and FIGS. 4(a) and (b) are, respectively, schematic perspective views of examples of the cylindrical body according to the present invention;

FIGS. 5(a) and (b) are respectively, diagrams for explaining the change of the λ controlling point, depending on the manner of the impingement of the gas to be measured on the measuring electrode; and FIGS. 6(a) and (b) are respectively, a schematic partial side view and a schematic cross sectional view of a conventional oxygen sensor.

Numberings in the Drawings

1 . . . measuring electrode, 2 . . . plate-shaped sensor element, 3 . . . protective cover, 4 . . . guide plate, 5 . . . gas inlet hole, 6 . . . cylindrical body, 7 . . . gas outlet hole, 8-1 to 8-5 . . . radial flange, 9 . . . lid, 10 . . . flange portion, 11, 12 . . . vane, 21 . . . plate-shaped sensor element, 22 . . . protective cover, 23 . . . gas vent hole, 24 . . . measuring electrode.

DESCRIPTION OF PREFERRED EMBODIMENTS

Hereinafter, the present invention will be explained in more detail with reference to the accompanying drawings which, however, should not be construed by any means as limitations of the present invention.

Referring to FIG. 1, a structure of an embodiment of the oxygen sensor of the present invention is shown. In this embodiment, a measuring electrode 1 of a heretofore known structure for measuring a gas to be measured is attached on the broader width surface of a plate-shaped sensor element 2, and the sensor element 2 is fixed on a not shown oxygen sensor body. The sensor element 2 is covered, for example, by a metallic protective cover 3. The metallic protective cover 3 is provided with a plurality of gas inlet holes 5 each having a guide plate 4. Between the protective cover 3 and the sensor element 2 is provided a columnar cylindrical body 6 having open end surfaces, in such a fashion as to cover the sensor element 2. The cylindrical body 6 does not have a gas vent hole on the side wall thereof. Even when the cylindrical body 6 has a gas vent hole or holes on the side wall thereof, the gas vent hole is arranged so as not to face the measuring electrode or so as not to be positioned in front of the measuring electrode 1. In this embodiment, the lower open end of the cylindrical body 6 opposite to the upper open end accommodating the sensor element 2, is fixed on the bottom of the protective cover 3.

Referring to FIGS. 2(a) and (b), another embodiment of the oxygen sensor of the present invention is shown, in which the same reference numbers with those of FIG. 1 represent the same ones with those of FIG. 1, so that explanations thereof are omitted below. The differences of the embodiment of FIGS. 2(a) and (b) from the embodiment of FIG. 1 are a change of the inner diameter of the cylindrical body 6 from the middle, a provision of a gas outlet hole 7 in the bottom surface of the protective cover 3, and a mechanical connection of the lower open end surface of the cylindrical body 6 to the gas outlet hole 7. Moreover, the cylindrical body 6 has radial flanges 8-1-8-4 which are connected to the inner wall surface of the protective cover 3, as shown in FIG. 2(b). In this embodiment, the gas to be measured is supplied through the plural gas inlet holes 5 via the guide plate 4, and flowed around the sensor element 2 downwardly from the plural gas inlet holes 5, so as to give an improved flow of the gas on the measuring electrode 1, as shown in FIG. 2(a).

Referring to FIGS. 3(a) and (b), other examples of the cylindrical body 6 according to the present invention are shown in perspective views. In the example shown in FIG. 3(a), the columnar shaped cylindrical body 6 has a lid 9 on the upper end surface thereof at the back side of the measuring electrode 2, so that the gas which is to be measured can hardly enter the back side of the measuring electrode 1. In the example shown in FIG. 3(b), the cylindrical body 6 has a half-circular shape in cross section, so that the space in the back side of the measuring electrode 1 is made rather small. In both examples shown in FIGS. 3(a) and (b), the response to the change of oxygen in the gas to be measured can be quickened.

Referring to FIGS. 4(a) and (b), other examples of the cylindrical body 6 according to the present invention have a flange portion 10 at its upper open end surface. In the example shown in FIG. 4(a), the flange portion 10 has a plurality of vanes 11. In the example shown in FIG. 4(b), the flange portion 10 has a plurality of vanes at the upper side wall of the cylindrical body 6 which corresponds to the cylindrical body 6 of FIG. 2(a) having a small diameter portion and a large diameter portion, at such positions that the vanes 12 do not face the gas inlet holes 5 of the protective cover 3. In both examples shown in FIGS. 4(a) and (b), the response to the change of oxygen in the gas to be measured can be improved, because the gas to be measured is quickly supplied to the measuring electrode 1 by virtue of the vanes 11 or 12. In these examples, penetration holes may be provided instead of the vanes 11 and/or 12, or the vanes 11 and/or 12 may be opened inwardly or outwardly.

As apparent from the foregoing descriptions, the oxygen sensor of the present invention is provided with a determined cylindrical body between the protective cover and the plate-shaped sensor element, so that the gas to be measured is impinged indirectly upon the measuring electrode always at a constant manner, regardless to an attached direction of the oxygen sensor. Thus, the oxygen sensor of the present invention always assures a constant λ controlling point and a constant measurement precision.

Although the present invention has been explained with specific embodiments, it is of course apparent to those skilled in the art that various changes and modifications thereof are possible without departing from the broad spirit and aspect of the present invention as defined below.

What is claimed is:

1. An oxygen sensor, comprising:
   a planar oxygen sensor element having a measuring electrode arranged on a broad width surface thereof;
   a protective cover surrounding the planar sensor element, said protective cover having gas inlet holes through which a gas to be measured is introduced into said protective cover and at least one gas outlet hole at a central portion of a bottom end thereof through which the gas exits said protective cover after measurement and having no gas vent hole on its side wall, said at least one gas outlet hole being defined by a wall member upwardly protruding from the bottom of said protective cover; and a cylindrical body provided between the protective cover and the planar oxygen sensor element, said cylindrical body having a first open end and a second open end opposed to said first open end, said second open end being fixed to said wall member upwardly protruding from the bottom of said protective cover;

wherein said cylindrical body isolates said planar oxygen sensor element from direct contact with the measurement gas.

2. The oxygen sensor of claim 1, wherein the cylindrical body has a small diameter portion and a large diameter portion connected to the small diameter portion.

3. The oxygen sensor of claim 1, wherein the cylindrical body has radial flanges connected to the protective cover.

4. The oxygen sensor of claim 1, wherein the cylindrical body has a lid on the upper end thereof at the side of the sensor element opposite the side where the measuring electrode is arranged.

5. The oxygen sensor of claim 1, comprising a flange portion with vanes at the top of the upper open end of the cylindrical body.

6. The oxygen sensor of claim 1, wherein the gas inlet holes of the protective cover consist of slits having guide plates.

* * * * *